(12) United States Patent
Tanaka et al.

(10) Patent No.: US 7,269,242 B2
(45) Date of Patent: Sep. 11, 2007

(54) X-RAY CT APPARATUS

(75) Inventors: Kazuhiro Tanaka, Ibaraki (JP);
Atsushi Hibino, Chiba (JP); Kuniyoshi Okabe, Chiba (JP); Masahiro Kanou, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/498,063

(22) PCT Filed: Dec. 9, 2002

(86) PCT No.: PCT/JP02/12857

§ 371 (c)(1),
(2), (4) Date: Jun. 9, 2004

(87) PCT Pub. No.: WO03/049616

PCT Pub. Date: Jun. 19, 2003

(65) Prior Publication Data

US 2004/0264624 A1 Dec. 30, 2004

(30) Foreign Application Priority Data

Dec. 10, 2001 (JP) .............................. 2001-375131

(51) Int. Cl.
*G21K 1/02* (2006.01)

(52) U.S. Cl. ............................................ 378/16; 378/4

(58) Field of Classification Search .................... 378/8, 378/20, 4, 11, 198, 15–16, 25, 38–40, 145, 378/147–148, 62, 196, 197, 191, 146
See application file for complete search history.

(56) References Cited

U.S. PATENT DOCUMENTS

| 5,095,501 | A | * | 3/1992 | Kobayashi .................. 378/196 |
| 6,118,842 | A | * | 9/2000 | Arai et al. ..................... 378/39 |
| 6,125,163 | A | * | 9/2000 | Barth et al. ..................... 378/4 |
| 6,188,744 | B1 | * | 2/2001 | Shinohara et al. ............. 378/8 |
| 6,222,906 | B1 | * | 4/2001 | Sakaguchi et al. ......... 378/98.8 |
| 6,246,742 | B1 | * | 6/2001 | Besson et al. ................. 378/8 |
| 6,574,304 | B1 | * | 6/2003 | Hsieh et al. .................. 378/62 |
| 2002/0048347 | A1 | * | 4/2002 | Saito .......................... 378/207 |
| 2002/0141531 | A1 | * | 10/2002 | Taguchi ...................... 378/19 |

FOREIGN PATENT DOCUMENTS

| JP | 3-234242 | 10/1991 |
| JP | 10-136261 | 5/1998 |
| JP | 10-162990 | 6/1998 |
| JP | 2001-120534 | 5/2001 |

* cited by examiner

*Primary Examiner*—Hoon Song
(74) *Attorney, Agent, or Firm*—Antonelli, Terry, Stout & Kraus, LLP.

(57) ABSTRACT

An X-ray CT apparatus is capable of obtaining an image of arbitrary size for an arbitrary part of an object to be examined. The X-ray CT apparatus prepares two-dimensional data and three-dimensional data from a plurality of X-ray information obtained by driving an X-ray tube and an X-ray information detector through one rotation around a patient in a range between a lower jaw and the eyes of the patient, and it displays a tomographic image based thereon on a display unit. A rotational mechanism is fitted to a support, a U-shaped arm is mounted on the support with the X-ray tube and the X-ray information inputting means facing each other and fitted, and the image of an arbitrary size of an arbitrary part of the patient is collected and displayed as the patient is supported in a chair which is capable of being electrically-driven in the vertical direction.

19 Claims, 5 Drawing Sheets

X-RAY CT APPARATUS

TECHNICAL FIELD

The present invention relates to an X-ray CT apparatus, which radiates X-rays to a portion of an object to be examined and processes a projection image thereof to create a tomogram; more particularly, the invention relates to an X-ray CT apparatus which can create a tomogram on a portion of a patient which is undergoing dental care.

BACKGROUND OF THE INVENTION

In dental care, general imaging in which film is positioned in back of teeth to perform X-ray imaging, panoramic imaging which involves simultaneously rotating an X-ray tube and film, cephalometric imaging in which an X-ray tube is greatly detached from the film during imaging, and the like are available. However, because all of these procedures involve simple X-ray imaging, only a plane image is obtainable.

Recently, a new type of dental surgery has been performed in which an implant is embedded into bone to fix artificial teeth to the jaw. When such surgery is performed, it is important to three-dimensionally observe the form of the teethridge and nearby bones. However, according to conventional X-ray imaging, it is impossible to three-dimensionally observe the form of teethridge and nearby bones, and so the form has to be determined on the basis of a plane image to perform surgery. Accordingly, the surgery requires more than normal skill, and there has been a problem in that a medical accident is likely to happen.

Such a problem can be solved by three-dimensionally observing the form of the teethridge and nearby bones using a conventional X-ray CT apparatus. The conventional X-ray CT apparatus does not image only one portion of a section of a body, such as a teethridge and nearby bones, but radiates X-rays to the whole area and obtains a tomogram of a desired portion from the obtained whole-area image. However, because the desired portion which forms the subject here is the form of the teethridge and the nearby bones, the image thereof becomes small compared with the entire image. Therefore, when the desired portion is small, the extracted image is small, and it is difficult to be recognize details since the image thereof is extracted from the entire image.

In this case, a tomogram of the desired portion can be easily imaged by constructing an X-ray CT apparatus which operates to radiate X-rays only to the desired portion and to create a projection image thereof. One example of an apparatus which radiates X-rays only to a desired portion to create a CT image thereof is described in Japanese Unexamined Patent Publication 2000-139902.

According to Japanese Unexamined Patent Publication 2000-139902, because X-rays are locally radiated to a local portion by using an X-ray cone beam collimator, prevention of excessive radiation exposure of the object is taken into consideration. However, in operations for selecting whether a tomogram of one tooth being a lesion is created or that of a whole jaw is created, for example, the collimator of an X-ray generator has to be set in every imaging operation, which makes the selecting operation complicated. Therefore, it is difficult to image an arbitrary portion of arbitrary size in an object. This problem is not taken into consideration at all in Japanese Unexamined Patent Publication 2000-139902.

An object of the present invention is to provide an X-ray CT apparatus which can image an arbitrary portion of an arbitrary size in an object.

SUMMARY OF THE INVENTION

To achieve the above-stated object, an X-ray CT apparatus according to the invention includes: an X-ray generating means for generating X-rays; an X-ray detecting means arranged opposite to the X-ray generating means for two-dimensionally detecting a dose of X-rays passing through an object to be examined; means for holding the X-ray generating means and the X-ray detecting means so that the object is placed therebetween; rotation driving means for driving the holding means to rotate around the object; image processing means for producing a tomogram of the object on the basis of the X-ray dose detected by the X-ray detecting means; and display means for displaying the tomogram, further including means for changing the size of the field of view (FOV) in accordance with a detected portion of the object displayed on the display means.

Specifically, if the FOV size is set for one tooth, a tomogram of one tooth is created by image processing means from the X-ray dose based on a one-tooth FOV size, and the tomogram is displayed by the display means. If the FOV size is set for a whole jaw, a tomogram of the whole jaw is created by the image processing means from the X-ray dose based on a whole-jaw FOV size, and the tomogram is displayed by the display means. Thus, when the whole jaw or one tooth is imaged, an arbitrary portion of arbitrary size in the object can be imaged.

Further, the FOV size changing means includes X-ray converting means for converting the X-rays into visible light; light receiving means for converting the visible light converted by the X-ray converting means into electrical signals; and means for changing a portion of the visible light of the X-ray converting means necessary for creating the tomogram.

This is involved with the specific structure of the X-ray detecting means, which includes X-ray converting means, such as an image intensifier device, light receiving means, such as a CCD camera, and an optical system which forms an image of the image intensifier device on the CCD camera. The optical system includes an electric collimator for adjusting the amount of light. When various areas are imaged, the optical system adjusts the size of the image and the brightness of the electric collimator, thus an optimum CT image can be obtained.

Further, the X-ray detecting means is a two-dimensional X-ray flat sensor, and the FOV size changing means includes means for changing the region necessary for creating the tomogram using electrical signals converted by the two-dimensional X-ray flat sensor.

This is involved with the specific structure of the X-ray detecting means, in which an two-dimensional X-ray flat sensor is employed instead of the image intensifier and the CCD camera. According thereto, even when various areas are imaged, the image size is adjusted by shutting off electrical signals of an unnecessary area and the image brightness displayed, while changing the amplification of the two-dimensional X-ray flat sensor elements, thereby an optimum CT image can be obtained.

The FOV size changing means includes means for inputting a desired FOV size by moving a cursor of a pointing device to an FOV size changing switch displayed on the display means and control means for changing the FOV size to the size input by the input means. Thus, the input of an FOV change can be certainly and promptly set by operating the FOV changing switch displayed on a monitor of the display means.

Further, by controlling the conditions of X-ray generation of the X-ray generating means in accordance with the FOV size designated by the FOV size changing means, an image of the input X-ray dose can be obtained under more preferable X-ray conditions of the X-ray detecting means changed due to the change of the FOV size, with adjustment of the tube voltage, the tube current, and the radiation time of the X-ray generator.

Further, the apparatus includes means for adjusting the size of the tomogram displayed by the display means. Thus, a portion having an arbitrary size can be imaged.

Further, the adjusting means includes means for adjusting the distance between the X-ray generating means and the X-ray detecting means on the holding means. Thus, since the radiation field of the X-ray generating means is fixed, by properly adjusting the distance between the X-ray generating means and the X-ray detecting means to bring them close to or keep them away from each other, an arbitrary FOV size can be freely chosen. Therefore, the portion which needs to be examined by a doctor can be enlarged. By adjusting the distance in accordance with the size of an element of the optical system or of the two-dimensional flat sensor, highly accurate adjustment can be carried out.

Further, the adjusting means is designed to adjust the distance between the X-ray generating means and the X-ray detecting means by extending and retracting a part of the holding means. Thus, when the X-ray generating means and the X-ray detecting means are mounted on the distance adjusting means, the distance therebetween can be adjusted by extending and retracting a part of the distance adjusting means.

Further, the holding means has a U-shaped arm and is provided with the X-ray generating means and the X-ray detecting means on opposite ends of the arm, and the rotation driving means is designed to rotate the U-shaped arm around its intermediate portion. This is involved with the specific structure of the X-ray CT apparatus, in which the X-ray generating means and the X-ray detecting means are respectively provided on the opposite ends of the U-shaped arm, and X-rays are radiated from the X-ray generating means to the X-ray detecting means between the ends of the U-shaped arm. The rotation driving means rotates X-rays around the object by rotating the U-shaped arm around its intermediate portion, thus a fluoroscopic image necessary for creating a tomogram can be obtained.

Further, the apparatus includes means for extending a tomogram of the FOV size that has been changed by the FOV size changing means. By switching the FOV size, both the whole face and a single tooth can be enlarged in the image, whereby it becomes easy to formulate a treatment plan for implant surgery and to observe a passage after the surgery.

The apparatus includes means for determining the position of the object so that an arbitrary region of the object is located at the rotation center of the X-ray generating means and the X-ray detecting means. When the object is a human body, it is necessary to finely adjust the imaging position of the chair which supports the patient in accordance with the difference of his/her seated height and the portion to be imaged. Here, the position can be freely determined in a three-dimensional space by electrically moving the object up and down, back and forth, and from side to side, or by rotating the patient. Further, when the head is imaged, the imaging position thereof can be determined by moving the head back and forth and from side to side or by rotating it in accordance with the shape thereof.

BEST MODE FOR CARRYING OUT THE INVENTION

Figure 1:
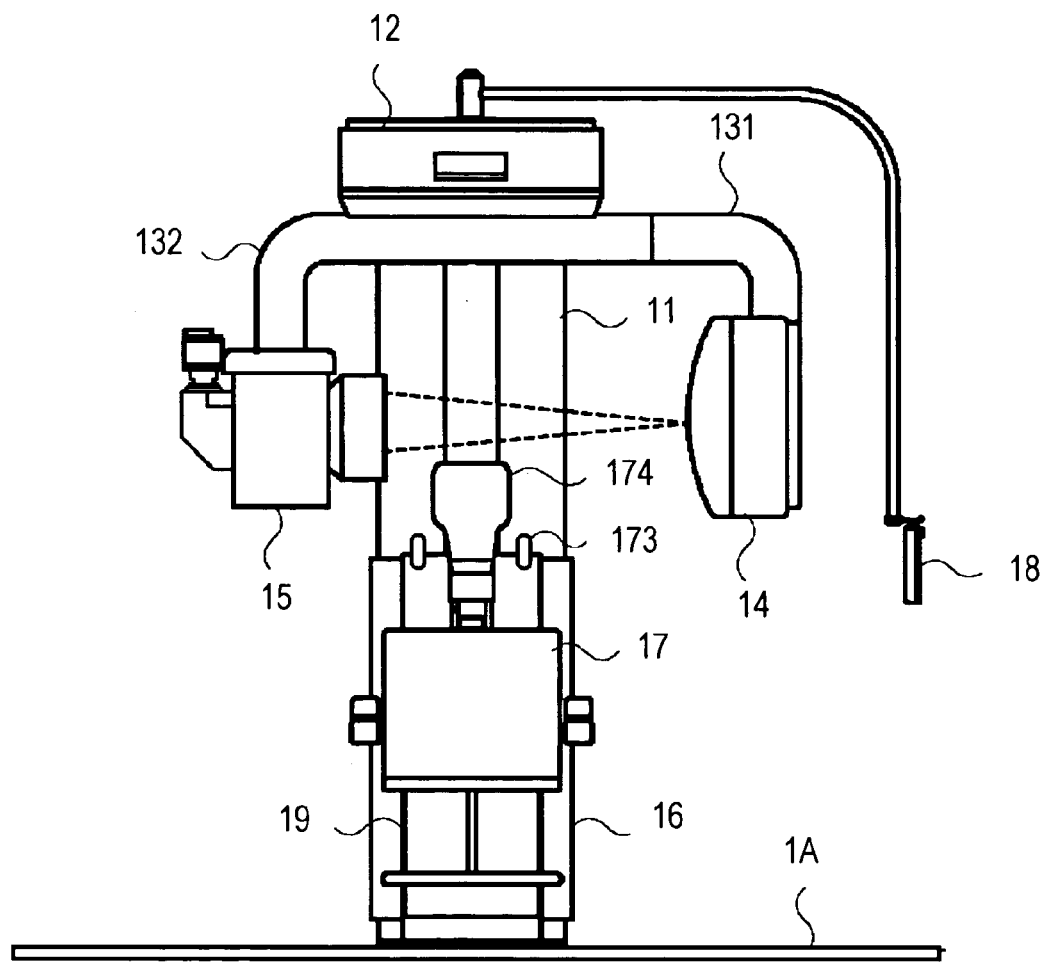
FIG. 1 is a front view of a scanner mechanism unit of an X-ray CT apparatus according to one embodiment of the invention.

Hereinafter, a preferred embodiment of an X-ray CT apparatus according to the present invention will be described with reference to the accompanying drawings. The X-ray CT apparatus according to the invention includes a scanner mechanism unit 1 and an image processing unit 2. FIG. 1 shows the scanner mechanism unit 1 of the X-ray CT apparatus according to one embodiment of the invention.

The scanner mechanism unit 1 includes a column 11, a U-shaped support rotation driving unit 12, arms 131 and 132 that form the U-shaped support, X-ray generator 14, X-ray information inputting means (detector) 15, control means 16, a chair 17 for the patient, a console 18, a chair driving device 19, and a mat switch 1A. The column 11 has a reverse L shape and has the U-shaped support driving unit 12 mounted on end thereof. The U-shaped support driving unit 12 holds the suspended arms 131 and 132 and rotates the arms 131 and 132 at a predetermined speed with respect to the end of the reverse L-shaped column 11, which constitutes a rotation center.

The X-ray generator 14 is designed to generate X-rays, and it is provided on one end of the arm 131. The X-ray information detector 15 is arranged opposite to the X-ray generator 14, and it is mounted on one end of the shaped arm 132. The detector 15 is designed to two-dimensionally detect an X-ray dose passing through the object. That is, the X-ray generator 14 is arranged opposite to the X-ray information detector 15 in relation to the U-shaped support constituted by arms 131 and 132. The U-shaped support constituted by arms 131 and 132 is driven to rotate by approximately 405 degrees around the end of the reverse L-shaped column 11, which constitutes the rotation center, by the U-shaped support rotation driving unit 12. Although the imaging range is 360 degrees, the rotation range is set to be wider by 45 degrees so as to begin imaging from the point where the rotation speed becomes constant.

Figure 5:
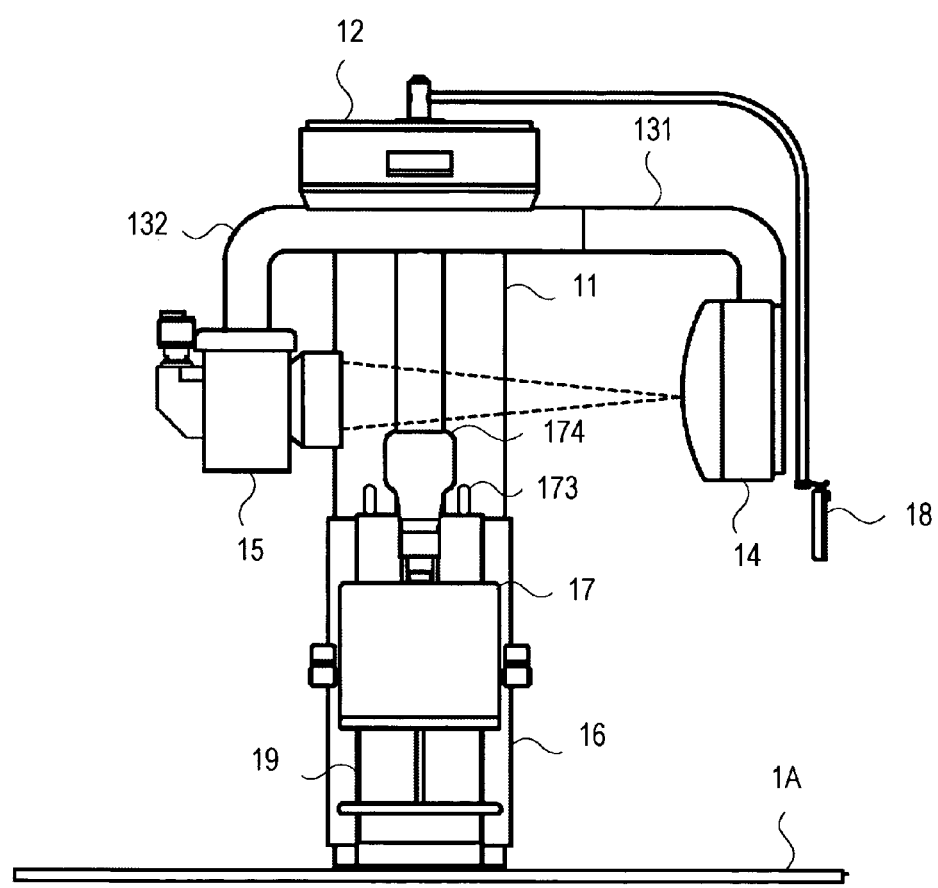
FIG. 5 is a diagram showing change in the appearance of an X-ray CT apparatus when a relatively large region is imaged.

Further, the arm 131 of the U-shaped support can be freely extended and retracted in a radius direction by sliding inside the arm 132, and thus the distance between the X-ray generator 14 and the X-ray information detector 15 is adjusted. FIG. 5 illustrates the state in which the arm 131 is extended to the maximum, and FIG. 1 illustrates the state in which it is retracted to the maximum. After the beginning of imaging, the X-ray generator 14 radiates X-rays in pulses in synchronism with image collection to reduce the X-ray exposure. The timing thereof is controlled by a position detection encoder built in the U-shaped support rotation driving unit 12.

Figure 4:
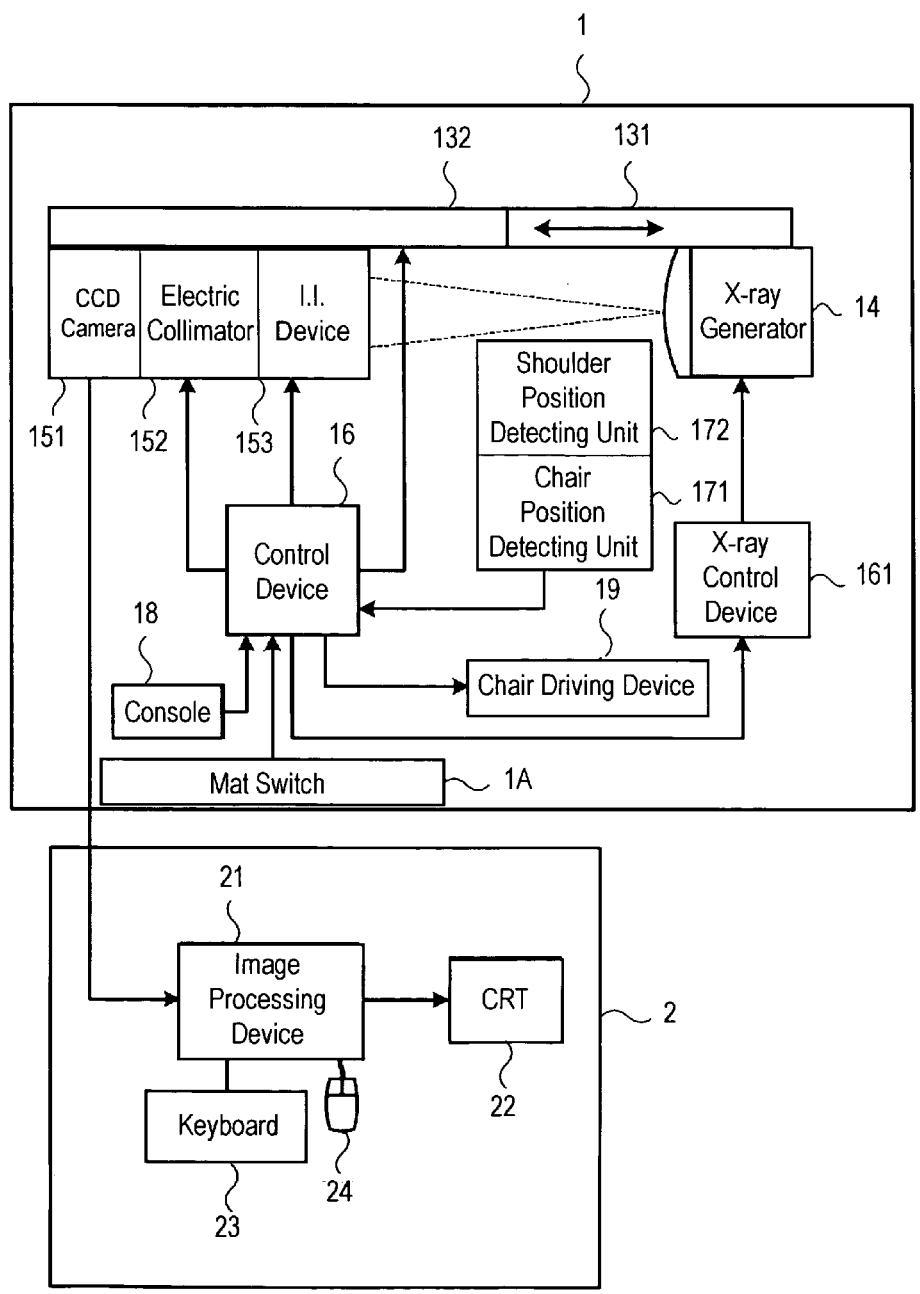
FIG. 4 is a block diagram schematically showing the structure of an X-ray CT apparatus according to one embodiment of the invention.

As seen in FIG. 4, the X-ray information detector 15 includes a CCD camera 151, an electric collimator 152, and an image intensifier device 153. The device 153 converts incident X-rays passing through the object into visible light. The CCD camera 151 receives the visible light converted by the device 153 and converts it into electrical signals. The X-ray information detector 15 can switch the imaging range in accordance with the imaging portion. The optical system is constructed so that the FOV size is set to be small when teeth are imaged, and it is set to be large when the jaw and face of a patient are imaged. By switching the FOV size, both the whole face and a single tooth can be enlarged in the image, whereby it becomes easy to establish the treatment plane of implant surgery and observe passage after the surgery. That is, in the X-ray information detector 15, the pixel size of the CCD camera 151 is changed by switching the FOV size of the image intensifier device 153 using the optical system including the electric collimator 152, whereby an FOV having a small size can be observed in detail.

The control device 16 for controlling the entire scanner mechanism unit 1 is provided below the column 11. The control unit 16 controls the X-ray conditions, the scanner mechanism unit 1, and the X-ray radiation according to control signals received from the image processing unit 2. Meanwhile, instead of the image intensifier device 153, an imaging plate, a two-dimensional flat X-ray sensor, and the like also may be used. Here, if a two-dimensional flat X-ray detector is used, X-rays can be directly converted into electrical signals without passing through a CCD camera or the like, which contributes to making the X-ray CT apparatus smaller and lighter.

When the FOV size is switched with the two-dimensional X-ray sensor, each element arranged in a direction of X-ray input is in a state of being activated or inactivated, and X-ray data is not obtained from the inactivated elements, but is obtained from the activated elements.

Figure 2:
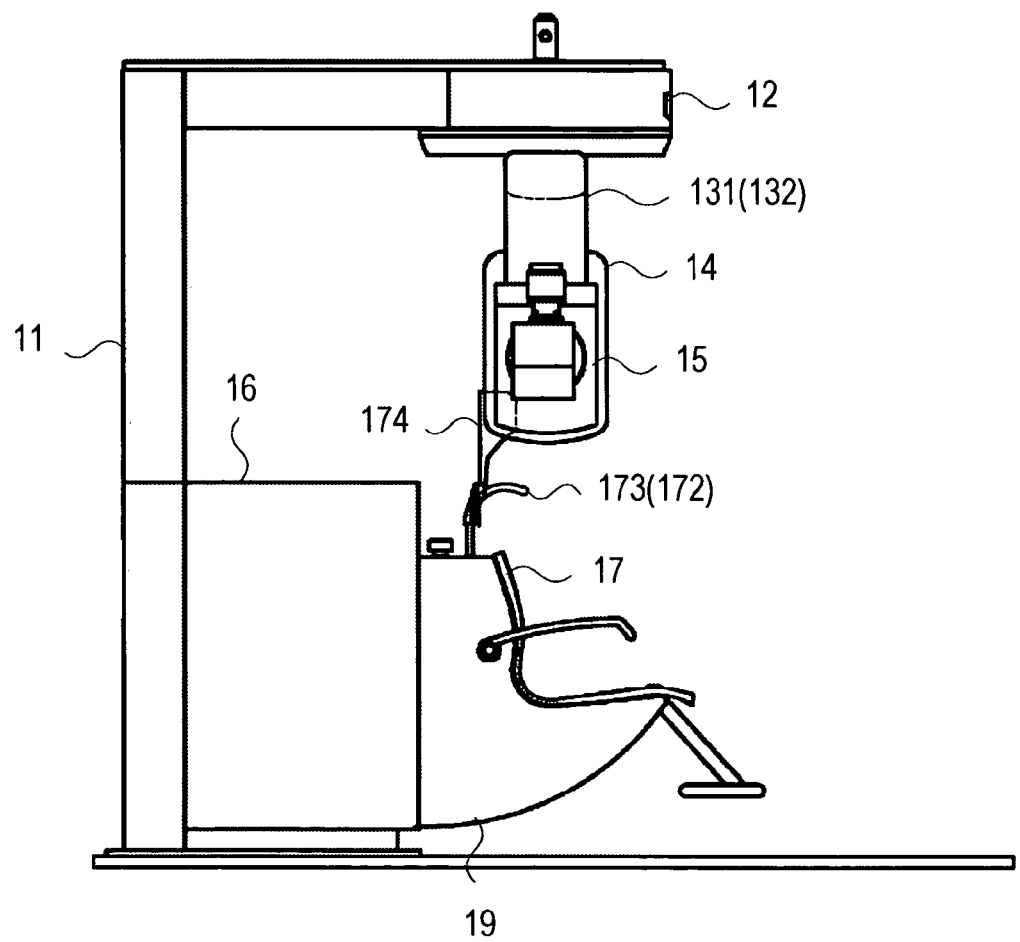
FIG. 2 is a left side view of FIG. 1.
Figure 3:
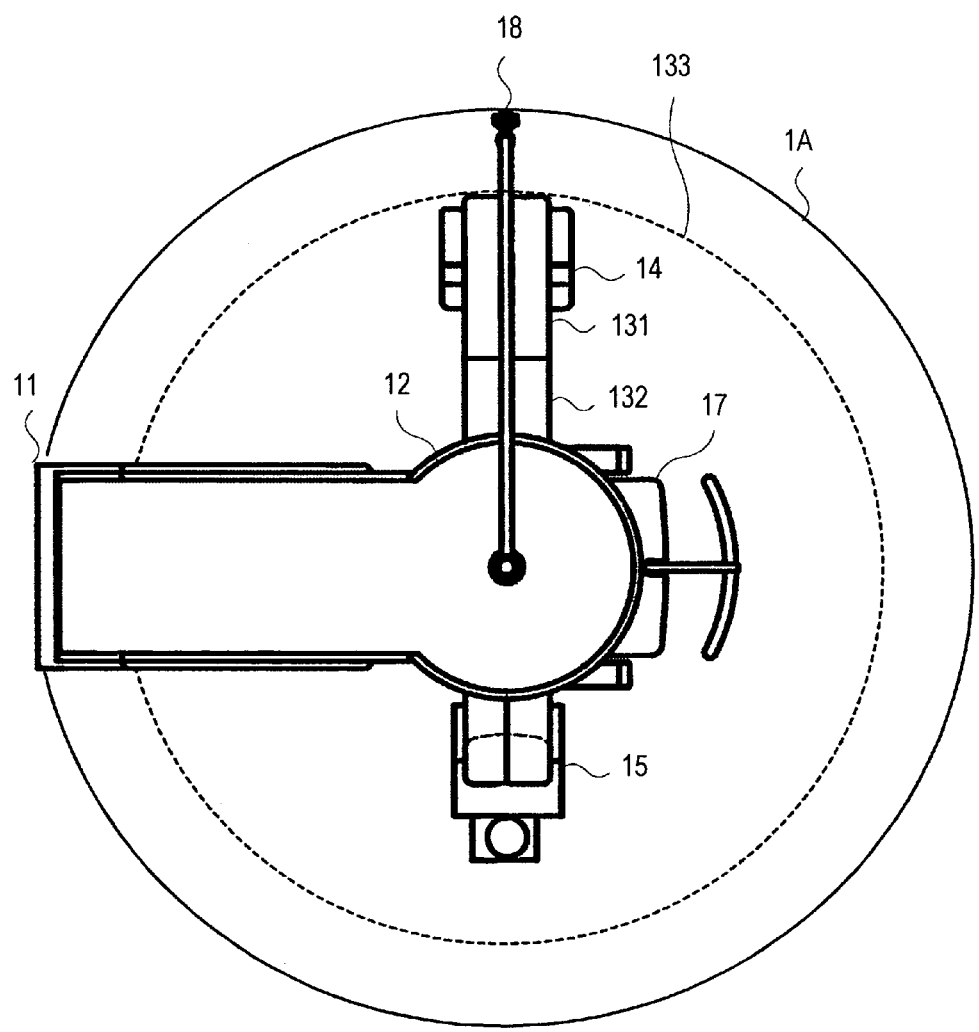
FIG. 3 is a top view of FIG. 1.

The chair 17 is provided so that the head of the patient is located on a rotation center axis of the U-shaped support constituted by the arms 131 and 132. The chair 17 is attached to the side of the column 4, including the chair driving device 19 for adjusting the imaging position in response to a difference of seated heights of the patient and finely adjusting the imaging position in response to an imaging portion, which can be electrically moved freely in a three-dimensional space, i.e., up and down, back and forth, and from side to side. Further, the chair driving device 19 also can be moved in a three-dimensional space in X-, Y-, and Z-directions, and it can be driven to rotate around the head of the patient as a rotation center. The chair includes a chair position detecting unit 171 for detecting the height of its seat and a shoulder position detecting unit 172 for detecting the position of the shoulders of the patient so that the shoulders do not touch the rotating X-ray information 15. The chair position detecting unit 171 is not shown in FIG. 1 to FIG. 3. The chair 17 is provided with a shoulder pad 173 and a head pad 174. The shoulder pad 173 includes a built-in shoulder position detecting unit 172. Further, the shoulder pad 173 is designed to rotate upward by 90 degrees so as not to hinder the patient sitting in the chair 17. Position signals detected by the chair position detecting unit 171 and the shoulder position detecting unit 172 are transmitted to the control device 16 and are signal-processed there. When the distance between the shoulder pad 173 and the X-ray information detector 15 is reduced, an interlock is engaged so that the chair 17 cannot be lifted. The head pad 174 has a band or the like for fixing the head of the patient during imaging.

Further, the position at which the head pad 173 is attached can be moved back and forth and from side to side to move the imaging portion in accordance with the shape of the head. The mat switch 1A is a mat provided so as to surround a rotating area 133 of the U-shaped support constituted by the arms 131 and 132. When a person or something steps onto the mat switch 1A, it closes the interlock so that the arms 131 and 132 cannot rotate.

The image processing unit 2, as seen in FIG. 4, includes the image processing device 21, a CRT 22, a keyboard 23, a mouse 24, and a pointing device, such as a trackball and a touch panel. The image processing device 21 takes in 288 X-ray fluoroscopic images with a 360-degree FOV, reconstructs those images into a two-dimensional image, and displays the two-dimensional image on the monitor (CRT) 22. The image reconstruction performed by the image processing device 21 is a known technique of cone-beam CT, in which multiple vertical items of information can be read in during one rotation of the U-shaped support around a patient. By starting 3D display software built in the image processing device 21, a 3D image can be created and displayed on the basis of the information. Because the shape can be three-dimensionally understood, the image is useful in making a plan of implant surgery.

A method of switching the FOV size of this X-ray CT apparatus will be described. First, a cursor is moved onto an FOV size changing switch displayed on the monitor 22 by using the mouse 24. A selected FOV size is communicated from the image processing device 21 to the control unit 16. The control unit 16 outputs a change of X-ray conditions (tube voltage and tube current) on the basis of the instructed FOV size. Also, the control unit 16 outputs a signal to the electric collimator 152 for adjusting an FOV size switching signal of the image intensifier device 153 and the light amount of the CCD camera. In the image intensifier device 153, if the FOV size is reduced and the X-ray conditions are the same as in a large FOV size, the light amount output to the CCD camera decreases. Accordingly, the image displayed on the CRT becomes dark and its contrast is deteriorated. Therefore, it is necessary to improve the X-ray conditions and activate a collimator in the front of the CCD camera in an opening direction to display an image having the same contrast as that of a large FOV size.

More specifically, the setting of the FOV size changing switch between imaging of the shape of a whole jaw and imaging of a teethridge and nearby bones of one tooth will be described. Here, the FOV size of X-rays input into the image intensifier device 153 is set for the whole jaw, a tomogram of the whole jaw of the object is created by the image processing device 21 from an X-ray dose based on a radiation area of the whole jaw, and a tomogram of one tooth is displayed on the CRT 22. Further, the FOV size of X-rays input into the image intensifier device 153 is set for one tooth, a tomogram of one tooth of the object is created, and the tomogram of one tooth is displayed on the CRT 22. In this manner, when the whole jaw and one tooth are sequentially imaged, the resolution is not deteriorated, and so an image contributing to diagnosis is obtainable.

In addition, while the radiation field of the X-ray generator 14 is not moved, the X-ray generator 14 can be moved from the position shown in FIG. 5 toward the image intensifier device 153 by electrically or manually changing the arm length of the U-shaped supported constituted by the arms 131 and 132 to which the X-ray generator is attached, as shown in FIG. 1, and thus, an arbitrary FOV size can be chosen. Accordingly, a portion needed for the examination by a doctor can be enlarged.

Further, to effect a change of the support length, a telescopic system utilizing a mechanism which changes the length of the support, as described in Japanese Unexamined Patent Publication Hei. 8-112272, is employed. If the system is electrically driven, a motor or the like is used. If the system is manually driven, an operator properly adjusts the extendable arm. The details of the mechanism are omitted here.

According to the above-described embodiment, by forming two-dimensional or three-dimensional data in an area from the lower jaw to the eyes of a patient, an image can be displayed, and so three-dimensional observation can be performed for evaluation of the lower jaw before surgery and following surgery. Therefore, a medical accident in implant surgery can be prevented and the diagnostic efficiency can be improved. Further, a panoramic image and a cephalometric image obtained in conventional X-ray imaging also can be displayed and simultaneously used with a three-dimensional image, whereby a more accurate diagnosis can be conducted.

The above-described embodiment has been directed to the case of using an X-ray CT apparatus in which two-dimensional and three-dimensional data in an area from the lower jaw to the eyes are formed, and a tomogram is created based on such data. However, it is possible to similarly apply the embodiment to a conventional X-ray CT apparatus.

As described above, by using an X-ray CT apparatus according to the present invention, an arbitrary portion of arbitrary size in a patient can be imaged.

The invention claimed is:

1. An X-ray CT apparatus comprising:
X-ray generating means for generating X-rays;
X-ray detecting means arranged opposite to the X-ray generating means for two-dimensionally detecting a dose of X-rays passing through an object to be examined;
means for holding the X-ray generating means and the X-ray detecting means so that the object is located therebetween;
means for adjusting a distance between the X-ray generating means and the X-ray detectinci means on the holdinci means;
rotation driving means for driving the holding means to rotate around the object;
image processing means for producing a tomogram of the object based on the X-ray dose detected by the X-ray detecting means;
display means for displaying the tomogram; and
means for changing an FOV size of the X-ray detecting means so as to reduce the FOV size of the X-ray detecting means to less than a maximum FOV size of the X-ray detecting means in accordance with a detected portion of the object displayed by the display means;
wherein the FOV size changing means includes X-ray converting means for converting the X-rays into visible light; light receiving means for converting the visible light converted by the X-ray converting means into electrical signals; and means for changing a portion of the visible light converted by the X-ray converting means necessary for creating the tomogram.

2. An X-ray CT apparatus according to claim 1, wherein the FOV size changing means includes means for inputting a desired FOV size by moving a cursor of a pointing device onto an FOV size changing switch displayed on the display means and control means for changing an FOV size to the size input by the inputting means.

3. An X-ray CT apparatus according to claim 1, wherein the adjusting means adjusts a size of the tomogram displayed by the display means.

4. An X-ray CT apparatus according to claim 3, further including means for expanding the tomogram obtained with the FOV size changed by the FOV size changing means.

5. An X-ray CT apparatus according to claim 1, wherein the adjusting means adjusts the distance between the X-ray generating means and the X-ray detecting means by extending and retracting a part of the holding means.

6. An X-ray CT apparatus according to claim 1, wherein the holding means is a U-shaped arm which is adjustable by the adjusting means and is provided with the X-ray generating means and the X-ray detecting means respectively on the ends, and the rotation driving means rotates the holding means around an intermediate portion of the U-shaped arm being the center.

7. An X-ray CT apparatus according to claim 1, further comprising means for determining a position of the object so that an arbitrary portion of the object is located on the rotation center of the X-ray generating means and the X-ray detecting means.

8. An X-ray CT apparatus according to claim 1, wherein the maximum FOV size is based upon the detection of actual data and the FOV size changing means reduces the FOV size to less than the maximum FOV size based upon detection of actual data.

9. An X-ray CT apparatus according to claim 1, wherein the FOV range changing means reduces the FOV size to less than the maximum FOV size while maintaining the same resolution as obtained with the maximum FOV size.

10. An x-ray CT apparatus according to claim 9, wherein the FOV size changing means maintains substantially the same contrast when the FOV size is reduced as obtained with the maximum FOV size of the X-ray detection means.

11. An X-ray CT apparatus comprising:
X-ray generating means for generating X-rays;
X-ray detecting means arranged opposite to the X-ray generating means for two-dimensionally detecting a dose of X-rays passing through an object to be examined;
means for holding the X-ray generating means and the X-ray detecting means so that the object is located therebetween;
means for adjusting a distance between the X-ray generating means and the X-ray detecting means on the holding means;
rotation driving means for driving the holding means to rotate around the object;
image processing means for producing a tomogram of the object based on the X-ray dose detected by the X-ray detecting means;
display means for displaying the tomogram; and
means for changing an FOV size of the X-ray detecting means so as to reduce the FOV size of the X-ray detecting means to less than a maximum FOV size of the X-ray detecting means in accordance with a detected portion of the object displayed by the display means;
wherein the X-ray detecting means is a two-dimensional X-ray flat sensor for converting X-rays into electrical signals, and the FOV size changing means includes means for changing a portion of the electrical signals converted by the two-dimensional X-ray flat sensor necessary for creating the tomogram.

12. An X-ray CT apparatus according to claim 3, wherein the adjusting means adjusts a size of the tomogram displayed by the display means.

13. An X-ray CT apparatus according to claim 3, wherein the adjusting means adjusts the distance between the X-ray generating means and the X-ray detecting means by extending and retracting a part of the holding means.

14. An X-ray CT apparatus comprising:
X-ray generating means for generating X-rays;
X-ray detecting means arranged opposite to the X-ray generating means for two-dimensionally detecting a dose of X-rays passing through an object to be examined;
means for holding the X-ray generating means and the X-ray detecting means so that the object is located therebetween;
means for adjusting a distance between the X-ray generating means and the X-ray detecting means on the holding means;
rotation driving means for driving the holding means to rotate around the object;
image processing means for producing a tomogram of the object based on the X-ray dose detected by the X-ray detecting means;
display means for displaying the tomogram,
means for changing an FOV size of the X-ray detecting means in accordance with a detected portion of the object displayed by the display means; and
means for controlling conditions of X-ray generation of the X-ray generating means in accordance with the FOV size changed by the FOV size changing means.

15. An X-ray CT apparatus according to claim 14, wherein the means for controlling conditions of X-ray generation of the X-ray generating means controls conditions of an X-ray generator of the X-ray generating means in accordance with the FOV size as changed by the FOV size changing means so that each of images obtained in a different FOV size has the same contrast.

16. An X-ray CT apparatus according to claim 15, wherein the means for controlling conditions of X-ray generation of the X-ray generating means controls conditions of the X-ray generator so that an image obtained at an imaging portion of interest has the same resolution as that of an image at a portion relating to the imaging portion.

17. An X-ray CT apparatus according to claim 14, wherein the means for controlling conditions of X-ray generation of the X-ray generating means controls conditions of an X-ray generator of the X-ray generating means so that an image obtained at an imaging portion of interest has the same contrast as that of an image at a portion related to the imaging portion.

18. An X-ray CT apparatus according to claim 5, wherein the adjusting means adjusts a size of the tomogram displayed by the display means.

19. An X-ray CT apparatus according to claim 5, wherein the adjusting means adjusts the distance between the X-ray generating means and the X-ray detecting means by extending and retracting a part of the holding means.

* * * * *